(12) United States Patent
Komoriya et al.

(10) Patent No.: US 7,105,618 B2
(45) Date of Patent: Sep. 12, 2006

(54) FLUORINE-CONTAINING POLYMERIZABLE MONOMERS AND POLYMERS, ANTI-REFLECTION FILM MATERIALS AND RESIST COMPOSITIONS USING SAME

(75) Inventors: Haruhiko Komoriya, Saitama (JP); Shinichi Sumida, Saitama (JP); Michitaka Otani, Austin, TX (US); Kazuhiko Maeda, Tokyo (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 10/316,183

(22) Filed: Dec. 11, 2002

(65) Prior Publication Data

US 2003/0232940 A1 Dec. 18, 2003

(30) Foreign Application Priority Data

Dec. 13, 2001 (JP) ............................. 2001-380776
Apr. 26, 2002 (JP) ............................. 2002-125505

(51) Int. Cl.
*C07C 33/46* (2006.01)
(52) U.S. Cl. ...................... 526/242; 526/245; 526/319; 526/346; 568/812
(58) Field of Classification Search ................ 526/242, 526/245, 319, 346; 568/812
See application file for complete search history.

(56) References Cited

U.S. PATENT DOCUMENTS

| 3,179,640 | A | * | 4/1965 | Middleton ................... 526/249 |
| 5,310,619 | A | * | 5/1994 | Crivello et al. .......... 430/270.1 |
| 6,383,620 | B1 | * | 5/2002 | Aoyama et al. ............. 428/212 |
| 2002/0155376 | A1 | * | 10/2002 | Hashimoto et al. ...... 430/270.1 |
| 2002/0164538 | A1 | * | 11/2002 | Allen et al. .............. 430/270.1 |
| 2004/0023176 | A1 | * | 2/2004 | Harada et al. .............. 430/907 |

FOREIGN PATENT DOCUMENTS

DE 4207261 A1 9/1993

OTHER PUBLICATIONS

Sprague et al., "the Synthesis and Attempted Polymerization of Trifluorostyrene Disubstituted by Hexafluoro-2-propanol Groups", Journal of Fluorine Chemistry, vol. 52, pp. 301-306 (1991).*
Moore, "A New Synthesis for a Highly Halogenated Styrene", Journal of Chemical and Engineering Data, vol. 15, No. 4, pp. 589-590 (1970).

* cited by examiner

Primary Examiner—David W. Wu
Assistant Examiner—Henry S. Hu
(74) Attorney, Agent, or Firm—Crowell & Moring LLP

(57) ABSTRACT

The present invention relates to a fluorine-containing polymerizable monomer having a structure of the general formula (1),

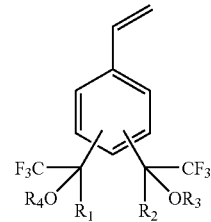

(1)

where each of $R_1$ and $R_2$ is independently a methyl group or trifluoromethyl group, and each of $R_3$ and $R_4$ is independently a hydrogen atom, an alkyl group, a fluorinated alkyl group, a ring structure having an aromatic ring, or an acid-labile protecting group, each of the alkyl group and the fluorinated alkyl group independently having a straight-chain, branched or ring form and having a carbon atom number of 1–25, each of $R_3$ and $R_4$ optionally and independently containing at least one of an oxygen atom and a carbonyl bond.

22 Claims, No Drawings

FLUORINE-CONTAINING POLYMERIZABLE MONOMERS AND POLYMERS, ANTI-REFLECTION FILM MATERIALS AND RESIST COMPOSITIONS USING SAME

BACKGROUND OF THE INVENTION

The present invention relates to (a) novel, fluorine-containing, styrene derivatives (monomers) containing a special structure, that is, a hydroxyl group or a substituent for protecting or modifying hydroxyl group, (b) polymers prepared by polymerization or copolymerization of such monomers, and (c) materials (e.g., anti-reflection coating materials and resist compositions) containing such polymers.

Fluorine-containing compounds have been used and developed in various fields particularly in the field of advanced materials due to their good qualities (e.g., water repellency, oil repellency, low water absorption, heat resistance, weather resistance, corrosion resistance, transparency, photosensitivity, low refractive index, and low dielectric property). In particular, there have been active researches and developments of fluorine-containing compounds in the fields of (a) anti-reflection films utilizing low refractive index and visible light transparency of fluorine-containing compounds and (b) resist compositions utilizing transparency of fluorine-containing compounds in ultraviolet region (particularly vacuum ultraviolet wavelength region). In these fields, the common task of designing polymers is to achieve adhesion to the substrate and high glass transition point (hardness), while achieving transparency at each wavelength for use by introducing as many fluorine atoms as possible into the polymer. Although there have been various proposals for increasing transparency at each wavelength by increasing the fluorine content in the polymer, there is no or very few proposals for improving water repellency and adhesion and for obtaining higher glass transition point by newly designing fluorine-containing monomers themselves. Recently, there have been some reports of hydroxyl group-containing and fluorine-containing styrenes and hydroxyl group-containing and fluorine-containing norbornene compounds in the field of the next generation $F_2$ resist in vacuum ultraviolet region. However, there are demands for new materials (i.e., novel polymers and novel monomers for providing novel polymers) having a sufficiently low refractive index necessary for anti-reflection films.

SUMMARY OF THE INVENTION

It is an object of the present invention to provide a novel polymerizable monomer capable of providing a polymer that has (a) high transparency and low refractive index in a wide wavelength region from vacuum ultraviolet region to optical communication wavelength region, (b) improved adhesion to the substrate, (c) improved film forming property, and (d) improved etching resistance.

It is another object of the present invention to provide a process for producing the monomer.

It is still another object of the present invention to provide the polymer prepared by polymerization or copolymerization of the monomer.

It is a further object of the present invention to provide an anti-reflection coating material or resist composition prepared by using the polymer.

According to the present invention, there is provided a fluorine-containing polymerizable monomer having a structure of the general formula (1),

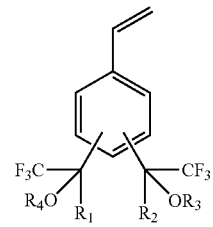

(1)

where each of $R_1$ and $R_2$ is independently a methyl group or trifluoromethyl group, and each of $R_3$ and $R_4$ is independently a hydrogen atom, an alkyl group, a fluorinated alkyl group, a ring structure having an aromatic ring, or an acid-labile protecting group, each of the alkyl group and the fluorinated alkyl group independently having a straight-chain, branched or ring form and having a carbon atom number of 1–25, each of $R_3$ and $R_4$ optionally and independently containing at least one of an oxygen atom and a carbonyl bond.

According to the present invention, there is provided a process for producing the fluorine-containing polymerizable monomer. This process comprises the steps of:

(a) reacting a benzene derivative, represented by the general formula (4), with an ethylation agent in the presence of a Lewis acid catalyst or protonic acid catalyst, thereby producing an ethyl benzene derivative represented by the general formula (5);

(b) reacting the ethyl benzene derivative with bromine, thereby producing a compound represented by the general formula (6); and (c) pyrolyzing the compound of the general formula (6) into the monomer of the general formula (1),

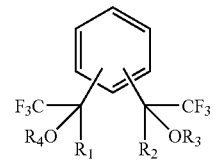

(4)

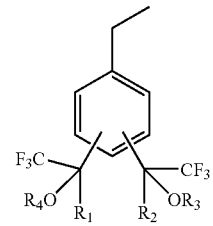

(5)

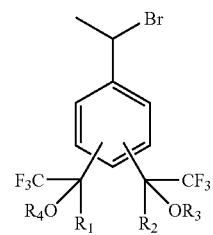

(6)

where $R_1$ to $R_4$ of the general formulas (4)–(6) are defined as in the general formula (1).

According to the present invention, there is provided a polymer prepared by polymerizing or copolymerizing the monomer of the general formula (1).

According to the present invention, there is provided an anti-reflection coating material or resist composition, comprising the polymer.

DESCRIPTION OF THE PREFERRED EMBODIMENTS

The above-mentioned novel polymerizable monomer according to the present invention is a fluorine-containing styrene derivative having a high fluorine content and a hydroxyl group(s) or a substituent(s) ($R_3$ and/or $R_4$) for protecting or modifying the hydroxyl group(s). The inventors unexpectedly found that polymers prepared by polymerization or copolymerization using the novel polymerizable monomer have (a) high transparency and low refractive index in a wide wavelength region from vacuum ultraviolet region to optical communication wavelength region, (b) improved adhesion to the substrate, (c) improved film forming property, and (d) improved etching resistance. Therefore, the resulting polymers are very useful for anti-reflection coating materials and resist compositions. Furthermore, the polymerizable monomer, which is a styrene monomer, is easy to be handled in an industrial scale production.

The fluorine-containing polymerizable monomer having a structure of the general formula (1) may specifically have a structure of the general formula (2) or (3):

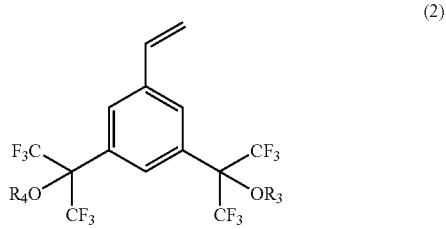

(2)

where $R_3$ and $R_4$ are defined as in the general formula (1).

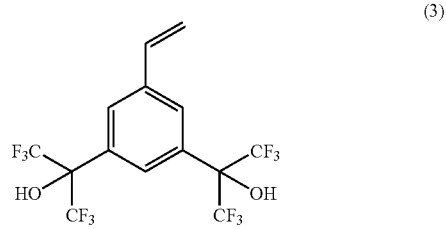

(3)

The fluorine-containing polymerizable monomer (a particular styrene derivative), which is represented by the general formula (1), (2) or (3), can be defined as being a compound in which two fluorine-containing carbinol groups (—$CH_2OH$) or their hydroxyl groups are protected by various functional groups. In particular, in case that the fluorine-containing polymerizable monomer is used for producing resist compositions, it is possible to protect the carbinol groups or their hydroxyl groups with fluorine-containing functional groups or acid-labile functional groups.

As stated above, each of $R_1$ and $R_2$ is independently a methyl group or trifluoromethyl group in the general formula (1). Therefore, the monomer of the general formula (1) can be defined as being a compound having a structure prepared by bonding hexafluoroacetone or trifluoroacetone to the benzene ring of styrene. In order to achieve low refractive index and high transparency (particularly in the ultraviolet wavelength region), both of $R_1$ and $R_2$ are preferably trifluoromethyl groups. With this, the monomer of the general formula (1) has a structure prepared by bonding hexafluoroacetone to the benzene ring of styrene.

As stated above, each of $R_3$ and $R_4$ is independently a hydrogen atom, an alkyl group, a fluorinated alkyl group, a ring structure having an aromatic ring, or an acid-labile protecting group. Each of the alkyl group and the fluorinated alkyl group independently has a straight-chain, branched or ring form and has a carbon atom number of 1–25. Each of $R_3$ and $R_4$ optionally and independently contains at least one of an oxygen atom and a carbonyl bond. Although the groups —$OR_3$ and —$OR_4$ are not particularly limited, these groups may be basically hydroxyl groups, which are the most simple in structure and are capable of providing high transparency. These hydroxyl groups can be modified with suitable substituents depending on the use of the resulting polymers. For example, the use of suitable substituents can provide the crosslinking property, the positive type photosensitivity (achieved by photoacid generator) and etching resistance for the purpose of having solubility in organic solvents and basic aqueous solutions, high glass transition point, and heat resistance in soldering. It is possible to use different substituents as $R_3$ and $R_4$ depending on the use of the resulting polymers.

The $C_1$–$C_{25}$ alkyl group used as $R_3$ or $R_4$ may be selected from methyl group, ethyl group, isopropyl group, n-propyl group, sec-butyl group, cyclopropyl group, cyclopentyl group, cyclohexyl group, ethylhexyl group, norbornel group, and adamantyl group. The fluorinated alkyl group is a group in which hydrogen atoms of the above alkyl group have been partially or fully replaced with fluorine atoms.

The groups $R_3$ and $R_4$ containing oxygen atom may be selected from linear ether groups (e.g., methoxymethyl ether (MOM) and methoxyethoxymethyl ether) and cyclic ethers (e.g., tetrahydrofuran and tetrahydropyrane). Those of a ring structure having an aromatic ring may be selected from phenyl group and 4-methoxybenzyl group. Those having a carbonyl group may be selected from acetyl group, propylcarbonyl group, pivaloyl group, hexylcarbonyl group, cyclohexylcarbonyl group, tert-butoxycarbonyl group (tert-BOC), benzoyl group, trifluoromethylcarbonyl group, perfluoropropylcarbonyl group, perfluoropivaloyl group, perfluorohexylcarbonyl group, and perfluorocyclohexylcarbonyl group.

The acid-labile protecting group is a protecting group that becomes labile or is released by an action of acid. The acid-labile protecting group may be selected from alkoxycarbonyl group, acetal group, silyl group, and acyl group. Examples of the alkoxycarbonyl group are tert-butoxycarbonyl group (t-BOC), tert-amyloxycarbonyl group, methoxycarbonyl group, ethoxycarbonyl group, and i-propoxycarbonyl group. Examples of the acetal group are methoxymethyl group (MOM), ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group, and ethoxyisobutyl group. Examples of the silyl group are trimethylsilyl group, ethyldimethylsilyl group, methyldiethylsilyl group, triethylsilyl group, i-propyldimethylsilyl group, methyldi-i-propylsilyl group, tri-i-propylsilyl group, t-butyldimethylsilyl group, methyldi-t-butylsilyl group, tri-t-butylsilyl group, phenyldimethylsilyl group, methyldiphenylsilyl group, and triphenylsilyl group. Examples of the acyl group are acetyl group, propionyl group, butyryl group, heptanoyl group, hexanoyl group, valeryl group, pivaloyl group, isovaleryl group, lauryloyl group, myristoyl group, palmiotyl group, stearoyl group, oxalyl group, malonyl group, succinyl group, glutaryl group, adipoyl group, piperoyl group, suberoyl group, azelaoyl group, sebacoyl group, acryoyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydratoropoyl group, cinnamoyl group, furoyl group, thenoyl group, nicotinoyl group, and isonicotinoyl group. Furthermore, these exemplary groups as the acid-labile protecting groups may be ones in which hydrogen atoms have been partially or fully replaced with fluorine atoms.

It is possible to produce the fluorine-containing polymerizable monomer of the general formula (1) by the above-mentioned process comprising the steps (a), (b) and (c). These steps can be expressed by the following reaction scheme.

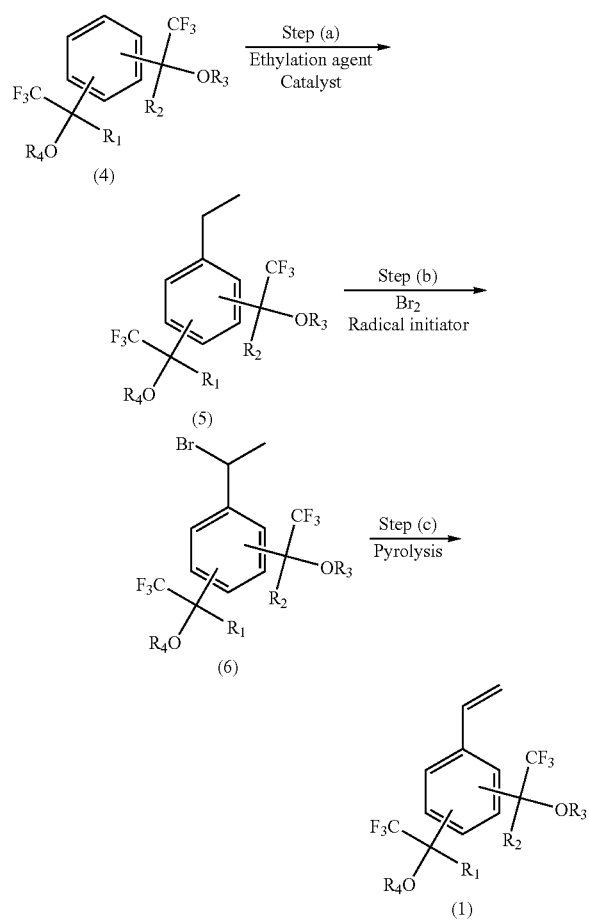

In the step (a), the ethylation agent may be selected from ethyl bromide, ethyl chloride, ethyl iodide, and ethyl fluoride. Of these, ethyl bromide is preferably used, since it can provide a suitable reaction rate. The ethylation agent may be in an amount of at least 1 mol per mol of the benzene derivative of the general formula (4). In view of the reaction rate and the yield of the ethylation product of the general formula (5), the ethylation agent is in an amount of preferably 1.1–20 moles, more preferably 1.5–10 moles, per mol of the benzene derivative of the general formula (4).

The acid catalyst used in the step (a) is a Lewis acid catalyst (e.g., aluminum chloride, aluminum bromide, gallium chloride, gallium bromide, ferric chloride ($FeCl_3$), zinc chloride, antimony chloride, titanium tetrachloride, tin tetrachloride, boron trifluoride, $Ti(OCH_3)_4$, $Ti(OC_2H_5)_4$, $Ti(OC_4H_9)_4$, $Ti(OCH(CH_3)_2)_4$, and $Zn(CH_3COO)_2 \cdot 2H_2O$) or a protonic acid catalyst (e.g., hydrogen fluoride, sulfuric acid, phosphoric acid, and hydrogen chloride). It is preferable to use a Lewis acid as the acid catalyst, since the target product can be obtained with high yield. Aluminum chloride is more preferably used, since it makes the reaction proceed smoothly and since it is easily available.

In the step (a), it is possible to use the acid catalyst in an amount of 0.1–10 moles per mol of the benzene derivative of the general formula (4). If it is less than 0.1 moles, the reaction rate and yield of the target ethylation product of the general formula (5) may become too low. Even if it is greater than 10 moles, it may not possible to further improve the yield. The acid catalyst is used in an amount of preferably 1–5 moles per mol of the benzene derivative of the general formula (4) to achieve a suitable reaction rate and a suitable yield.

Although the reaction temperature of the step (a) is not particularly limited, it can be from room temperature to 100° C. The reaction time can suitably be adjusted, since the reaction rate changes depending on, for example, the type and the amount of the catalyst and the reaction temperature. In fact, it is possible to continue the reaction until the benzene derivative of the general formula (4) is totally consumed, while the reaction solution is analyzed several times to determine the amount of the benzene derivative.

It is not particularly necessary to use reaction solvent in the step (a). It is, however, optional to add solvent for the purpose of controlling the reaction temperature and of deriving the benefit of handling easiness from the viscosity reduction of the reaction solution.

Although the post-treatment after the step (a) is not particularly limited, it is possible to isolate the target product by (1) extraction using organic solvent after the addition of the reaction solution to water or iced water or by (2) flash distillation.

The step (b) is a bromination of the ethyl benzene derivative of the general formula (5). This bromination can be (1) a first bromination in which the ethyl benzene derivative is reacted with bromine in the presence of a radical initiator or (2) a second bromination in which the ethyl benzene derivative is reacted with bromine by using light (in place of radical initiator) to produce radicals.

To conduct the first bromination, it is possible to add a radical initiator and bromine to the ethyl benzene derivative, followed by stirring and then heating. With this, the radical initiator is decomposed to produce radicals, and then the α-position carbon atom of the ethyl benzene derivative is selectively brominated into the compound of the general formula (6). Although the radical initiator is not particularly limited, it may be selected from azo compounds and peroxides. Of these, azobisisobutyronitrile (AIBN) is preferable in view of the reaction controllability. The amount of the radical initiator is not particularly limited. It may be 0.001–50 mol %, preferably 0.1–10 mol % in view of the reaction rate, based on the total mole numbers of the substrate (i.e., the ethyl benzene derivative).

In the first bromination, the reaction temperature may suitably be selected depending on the decomposition temperature of the radical initiator. It may be in a range of 0–50° C. The reaction time may be adjusted depending on the type of the radical initiator and the reaction temperature. The reaction may be terminated when the raw material has totally been consumed. The reaction time may be from 1 hr to 24 hr.

The step (b) can be conducted by using solvent. The solvent is not particularly limited as long as it does not react with bromine radicals. It may be selected from methylene chloride, carbon tetrachloride and chloroform.

The second bromination using light to produce bromine radicals can be conducted under conditions that are basically similar to the above-mentioned conditions of the first bromination. In the second bromination, it is preferable to use an ultraviolet lamp (e.g., high-pressure mercury lamp) as the light source. It is possible to irradiate the reaction solution with ultraviolet rays directly or from the outside of the reactor of Pyrex (trade name) to produce bromine radicals and thereby achieve the bromination. The reaction temperature for conducting the second bromination is preferably from 0° C. to 50° C. in view of the reaction controllability.

The step (c) is a step in which the brominated compound of the general formula (6) is pyrolyzed into the styrene derivative of the general formula (1) through debromination.

The step (c) can be conducted by a batch-wise or continuous operation. It is preferable to use a heating apparatus for continuous operation as the reaction apparatus in view of yield of the target product and productivity. In fact, it is possible to use a reaction apparatus that allows heating of the brominated compound at 100° C. and allows the target product to be taken out, since the debromination of the step (c) occurs at 100° C. or higher. In the case of the batch-wise operation, it is possible to use a reaction apparatus that is 5 similar to a vacuum distillation apparatus. The batch-wise operation can be conducted by putting the brominated compound of the general formula (6) into a distillation apparatus having a pressure of 100 mmHg or lower and then by heating the distillation apparatus at 100° C. or higher to distill the target product out.

The continuous operation of the step (c) can be conducted, for example, by gradually introducing the brominated compound of the general formula (6) into a reaction tube (heated at about 500° C.) through its one end and then by guiding the resulting styrene derivative of the general formula (1) into a cold trap through the other end of the reaction tube to collect the styrene derivative. In this case, it becomes possible to make the introduction of the brominated compound easy and to improve conversion by reducing the atmosphere of the reaction tube to have a pressure of 100 mmHg or lower. The reaction temperature of the continuous operation is preferably from 300 to 800° C. It is more preferably from 400 to 600° C. to obtain the styrene derivative of the general formula (1) with high yield. The way to introduce the brominated compound into the reaction apparatus is not particularly limited in the continuous operation. The brominated compound (liquid) can be introduced into a vertical-type reaction tube by a dropwise manner. Alternatively, the brominated compound (liquid) can be turned into vapor in a vaporization chamber, and then the obtained vapor can be introduced into the reaction tube of a vertical or horizontal type.

A polymer according to the present invention is a homopolymer of the monomer of the general formula (1), (2) or (3) or a copolymer prepared by copolymerization of the monomer of the general formula (1), (2) or (3) with another monomer (comonomer).

The polymer of the present invention can be a first copolymer having a repeating unit represented by the general formula (7).

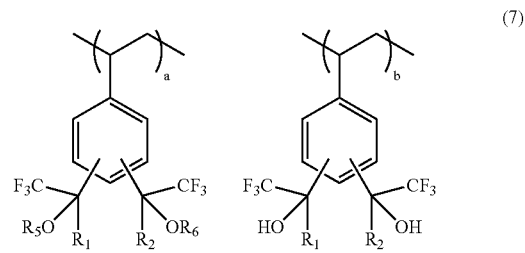

(7)

where $R_1$ and $R_2$ are defined as in the general formula (1), $R_5$ and $R_6$ are identical with $R_3$ and $R_4$ of the general formula (1) and optionally contain at least one of an oxygen atom and a carbonyl bond, at least one of $R_5$ and $R_6$ being the acid-labile protecting group, "a" and "b" are arbitrary integers, and "a:b" represents a copolymerization ratio in the copolymerization. In other words, "a:b" represents the ratio of the number of the left side repeating units of the general formula (7) to the number of the right side repeating units of the general formula (7) in the first copolymer. Hereinafter, "a:b" will be defined similarly.

It is needless to say that the acid-labile protecting group as at least one of $R_5$ and $R_6$ may be selected from the above-mentioned examples of alkoxycarbonyl group, acetal group, silyl group and acyl group. Furthermore, the exemplary groups as the acid-labile protecting groups may be ones in which hydrogen atoms have been partially or fully replaced with fluorine atoms.

The purpose of using the acid-labile protecting group is to make the polymer achieve (1) positive type photosensitivity and (2) dissolution in basic aqueous solution after irradiation with high-energy beam (e.g., far infrared radiation, excimer laser of 300 nm or less, and X-rays) or electron beam. The resulting polymer is further provided with transparency, if it contains a fluorine-containing functional group. Furthermore, the resulting polymer is further provided with etching resistance and high glass transition point, if it contains a cyclic structure.

The polymer of the present invention can be a second copolymer having a repeating unit represented by the general formula (8).

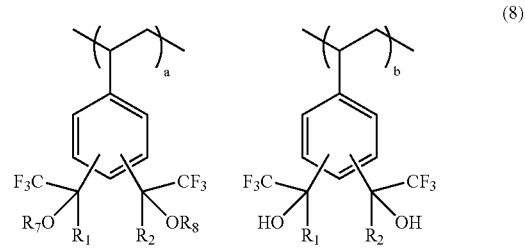

(8)

where $R_1$ and $R_2$ are defined as in the general formula (1), $R_7$ and $R_8$ are identical with $R_3$ and $R_4$ of the general formula (1) and optionally contain at least one of an aromatic ring, an oxygen atom and a carbonyl bond, each of $R_7$ and $R_8$ being the acid-labile protecting group, the alkyl group or the fluorinated alkyl group, at least one of $R_7$ and $R_8$ being the alkyl group or the fluorinated alkyl group, and "a" and "b" are arbitrary integers, and "a:b" represents a copolymerization ratio in the copolymerization.

The alkyl group as at least one of $R_7$ and $R_8$ may be selected from the above-mentioned examples of that as $R_3$ or $R_4$. The fluorinated alkyl group as at least one of $R_7$ and $R_8$ is a group in which hydrogen atoms of the alkyl group have been partially or fully replaced with fluorine atoms. Its examples are trifluoromethyl group, 2,2,2-trifluoromethylethyl group, and 1,1,1,3,3,3-hexafluoroisopropyl group.

The purpose of using the alkyl group or the fluorinated alkyl group as at least one of $R_7$ and $R_8$ is to make the polymer have a reduced hydrophilicity and an improved dissolution in organic solvent. The resulting polymer is further provided with transparency, if it contains a fluorine-containing functional group. Furthermore, the resulting polymer is further provided with etching resistance and high glass transition point, if it contains a cyclic structure.

Another monomer, which is to be copolymerized with the monomer of the general formula (1), (2) or (3), may be at least one selected from acrylic esters, methacrylic esters, fluorine-containing acrylic esters, fluorine-containing methacrylic esters, styrene, styrene derivatives (styrene compounds), fluorine-containing styrene derivatives (styrene compounds), vinyl ethers, fluorine-containing vinyl ethers, olefins, fluorine-containing olefins, norbornene, norbornene derivatives (norbornene compounds), and fluorine-containing norbornene derivatives (norbornene compounds).

Exemplary (meth)acrylic esters (i.e., acrylic esters and methacrylic esters) for the above-mentioned another monomer are not particularly limited with respect to their ester side chains. They are (meth)acrylic alkyl esters such as methyl (meth)acrylate, ethyl (meth)acrylate, n-propyl (meth)acrylate, isopropyl (meth)acrylate, n-butyl (meth) acrylate, isobutyl (meth)acrylate, n-hexyl (meth)acrylate, n-octyl (meth)acrylate, 2-ethylhexyl (meth)acrylate, lauryl (meth)acrylate, 2-hydroxyethyl (meth)acrylate, and 2-hydroxypropyl (meth)acrylate; (meth)acrylates containing groups such as ethylene glycol, propylene glycol and tetramethylene glycol; unsaturated amides such as (meth) acrylic amide, N-methylol(meth)acrylic amide, and diacetoneacrylic amide; (meth)acrylonitrile, alkoxysilane-containing vinyl silanes and (meth)acrylic esters, t-butyl (meth)acrylate, and cyclic (meth)acrylate such as 3-oxocyclohexyl (meth)acrylate, adamantyl (meth)acrylate, alkyladamantyl (meth)acrylate, cyclohexyl (meth)acrylate, tricyclodecanyl (meth)acrylate and (meth)acrylate having cyclic structures such as lactone ring and norbornene ring; and (meth)acrylic acid. Further examples are α-cyano group-containing (meth)acrylate and analogous compounds such as maleic acid, fumaric acid and maleic anhydride.

The fluorine-containing (meth)acrylic esters for the above-mentioned another monomer may have a fluorine-containing group at their α-position or ester moiety. Furthermore, they may have a cyano group at the α-position. Such fluorine-containing groups at their α-position may be trifluoromethyl group, trifluoroethyl group and nonafluoro-n-butyl group. In case that the fluorine-containing groups are contained at their α-position, their ester moiety is not necessarily required to have a fluorine-containing group. It may be preferable to use α-trifluoromethylacrylic alkyl ester as the above-mentioned another monomer, since it may become possible to provide a relatively high yield of the target polymer and an improved dissolution of the target polymer in organic solvent. It may be possible to provide the polymer with acid-decomposition property (i.e., property to be decomposed by an action of acid) by using trifluoromethylacrylic t-butyl ester (hereinafter TFMA-B). Such polymer has a possibility for use as resist composition.

Further exemplary fluorine-containing (meth)acrylic esters as the above-mentioned another monomer may have at their ester moiety a fluoroalkyl or perfluoroalkyl group or a fluorine-containing cyclic structure. This cyclic structure may have a substituent (e.g., fluorine and trifluoromethyl group), and its examples are fluorine-containing benzene ring, fluorine-containing cyclopentane ring, fluorine-containing cyclohexane ring, and fluorine-containing cycloheptane ring. Further exemplary (meth)acrylic esters may have at their ester moiety a fluorine-containing t-butyl ester group. It is optional to use (meth)acrylic esters having fluorine-containing functional groups at their ester moiety and α-position. Concrete examples of the fluorine-containing (meth)acrylic ester are 2,2,2-trifluoroethyl(meth) acrylate, 2,2,3,3-tetrafluoropropyl(meth)acrylate, 1,1,1,3,3,3-hexafluoroisopropyl(meth)acrylate, heptafluoroisopropyl (meth)acrylate, 1,1-dihydroheptafluoro-n-butyl(meth) acrylate, 1,1,5-trihydrooctafluoro-n-pentyl(meth)acrylate, 1,1,2,2-tetrahydrotridecafluoro-n-octyl(meth)acrylate, 1,1,2,2-tetrahydroheptadecafluoro-n-decyl(meth)acrylate, perfluorocyclohexylmethylacrylate, and perfluorocyclohexylmethylmethacrylate.

Further examples of the above-mentioned another monomer are styrene compounds and fluorine-containing styrene compounds, such as styrene, fluorinated styrene, hydroxystyrene, a compound in which a hexafluorocarbinol group(s) is bonded to the benzene ring, and styrene and hydroxystyrene each containing trifluoromethyl group substituted for hydrogen. These styrene compounds and fluorine-containing styrene compounds may have at their α-position a halogen, an alkyl group or a fluorine-containing alkyl group.

Still further examples of the above-mentioned another monomer are vinyl ethers, fluorine-containing vinyl ethers, allyl ethers, vinyl esters, and vinyl silanes. It is possible to copolymerize vinyl ethers, fluorine-containing vinyl ethers, allyl ethers and vinyl esters with the polymerizable monomer (represented by the general formulas (1), (2) or (3)) by suitably adjusting relative amounts of these monomers used in the copolymerization. For example, the another monomer may be an alkyl vinyl ether that optionally contains methyl group, ethyl group or hydroxyl group (e.g., hydroxyethyl group and hydroxybutyl group) and that optionally contains fluorine substituted for a part or all of the hydrogen atoms. The another monomer may be cyclohexyl vinyl ether or another cyclic vinyl ether containing hydrogen or carbonyl bond in its cyclic structure. Such cyclic vinyl ether may contain fluorine substituted for a part or all of the hydrogen atoms. Furthermore, allyl ethers, vinyl esters and vinyl silanes for the another monomer can be selected from known compounds without any particular limitation upon use.

Exemplary olefins for the above-mentioned another monomer are ethylene and propylene. Exemplary fluorine-containing olefins for that are vinyl fluoride, vinylidene fluoride, trifluoroethylene, chlorotrifluoroethylene, tetrafluoroethylene, hexafluoropropylene, and hexafluoroisobutene.

The above-mentioned norbornene compounds and fluorine-containing norbornene compounds as examples of the another monomer may have a mononucleus or multinucleus structure. It is possible to copolymerize these norbornene compounds with the above-mentioned polymerizable monomer of the general formula (1), (2) or (3), without any particular limitations. It is possible to prepare the norbornene compounds (e.g., 3-(5-bicyclo[2.2.1]heptane-2-yl)-1,1,1-trifluoro-2-(trifluoromethyl)-2-propanol) by a Diels-Alder addition reaction of unsaturated compounds (e.g., allyl alcohol, fluorine-containing allyl alcohol, homoallyl alcohol, fluorine-containing homoalcohol, acrylic acid, α-fluoroacrylic acid, methacrylic acid, and all of the above-mentioned (meth)acrylic esters and fluorine-containing (meth)acrylic esters) to dienes (e.g., cyclopentadiene and cyclohexadiene).

The above-mentioned another monomer may be a single monomer or a combination of at least two monomers. Upon the polymerization, the ratio of the polymerizable monomer to the another monomer is not particularly limited. The amount of the former is preferably from 10–100%, more preferably 30–100%. If it is less than 30%, the resulting polymer may become insufficient in transparency or film-forming property depending on the wavelength range for use.

The polymer of the present invention can be a third copolymer having a repeating unit represented by the general formula (9).

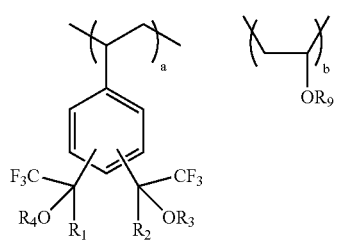

(9)

where $R_1$ to $R_4$ are defined as in the general formula (1), $R_9$ is an alkyl or fluorinated alkyl group having a carbon atom number of 1–25, having a straight-chain, branched or ring form, and optionally containing at least one of an aromatic ring, oxygen and a carbonyl bond, and "a" and "b" are arbitrary integers, and "a:b" represents a copolymerization ratio in the copolymerization.

The structure of $R_9$ is not particularly limited. Its preferable examples are alkyl groups (e.g., methyl group and ethyl group), fluoroalkyl groups having a trifluoroethyl group or $CnF_{2n+1}$, hexafluoroisopropyl group, cyclopentyl group, cyclohexyl group, norbornel group, adamantyl group, and butyl lactone group. These groups may have substituents (i.e., hydroxyl group and hexafluorocarbinol group). Specific examples of the vinyl ether, which forms the right side repeating unit of the general formula (9), may include methyl vinyl ether, ethyl vinyl ether, propyl vinyl ether, isopropyl vinyl ether, butyl vinyl ether, isobutyl vinyl ether, sec-butyl vinyl ether, t-butyl vinyl ether, pentyl vinyl ether, hexyl vinyl ether, octyl vinyl ether, and dodecyl vinyl ether. Further examples of the above-mentioned vinyl ether are perfluoroalkyl vinyl ethers such as perfluoromethyl vinyl ether, perfluoroethyl vinyl ether, perfluoropropyl vinyl ether, perfluoroisopropyl vinyl ether, perfluorobutyl vinyl ether, perfluoroisobutyl vinyl ether, perfluoro-sec-butyl vinyl ether, perfluoro-t-butyl vinyl ether, perfluoropentyl vinyl ether, perfluorohexyl vinyl ether, perfluorooctyl vinyl ether, and perfluorododecyl vinyl ether. Still further examples of the above-mentioned vinyl ether are hydroxyl-containing vinyl ethers such as hydroxymethyl vinyl ether, 2-hydroxyethyl vinyl ether, 3-hydroxypropyl vinyl ether, 4-hydroxybutyl vinyl ether, 5-hydroxypentyl vinyl ether, 6-hydroxyhexyl vinyl ether, diethylene glycol monovinyl ether, polyethylene glycol monovinyl ether, and 1,4-cyclohexanedimethanol vinyl ether.

The purpose of using the above-mentioned vinyl ether as the another monomer is to reduce aromatic rings and carbonyl bonds in the polymer and to make the polymer have a high transparency within a range of from the vacuum ultraviolet rays to the visible light rays. In particular, the purpose of using a fluorine-containing vinyl ether or hydroxyl-containing vinyl ether is to provide a novel fluorine-containing copolymer that is further improved, for example, in transparency, adhesion to the substrate, and film-forming property.

The polymer of the present invention can be a fourth copolymer having a repeating unit represented by the general formula (10).

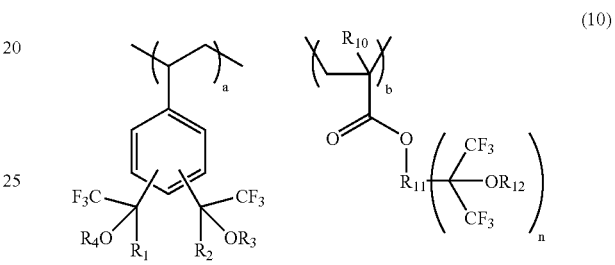

(10)

where $R_1$ to $R_4$ are defined as in the general formula (1), $R_{10}$ is a hydrogen atom, methyl group or trifluoromethyl group, $R_{11}$ is an alkyl group or a ring structure and optionally contains at least one of fluorine, oxygen and a carbonyl bond, the alkyl group having a carbon atom number of 1–25 and having a straight-chain, branched or ring form, the ring structure having an aromatic ring, $R_{12}$ is a hydrogen atom, an alkyl or fluorinated alkyl group or an acid-labile protecting group, the alkyl or fluorinated alkyl group having a carbon atom number of 1–25, having a straight-chain, branched or ring form, $R_{12}$ optionally containing at least one of an aromatic ring, oxygen and a carbonyl bond, "a" and "b" are arbitrary integers, and "a:b" represents a copolymerization ratio, and "n" is an integer of 1–3.

In the general formula (10), $R_{10}$ is preferably trifluoromethyl group in order to provide the fourth copolymer with low refractive index and high transparency (high transparency particularly in the ultraviolet wavelength region).

In the general formula (10), $R_{11}$ may be selected from straight-chain or branched alkyl groups, alkyl groups containing a ring structure, aromatic rings, and substituents formed by combining these. These groups may partially be fluorinated and may contain an unsaturated bond. Examples of $R_{11}$ are straight-chain or branched alkylene groups (such as methylene, ethylene, isopropylene and t-butylene), ring structures (such as cyclobutene, cyclohexane, norbornene, and adamantine groups), and phenyl group.

As stated above, $R_{12}$ in the general formula (10) may be a hydrogen atom, a hydrocarbon group (optionally branched), a fluorine-containing alkyl group, a ring structure containing an aromatic ring or aliphatic ring, or an acid-labile protecting group. Furthermore, $R_{12}$ may optionally contain oxygen or carbonyl bond. Although the group —$OR_{12}$ is not particularly limited, this group may be basically a hydroxyl group, which is the most simple in structure and is capable of providing high transparency. This hydroxyl group can be modified with suitable substituents depending on the use of the resulting polymers. Examples of such substituents ($R_{12}$) are $C_1$–$C_{25}$ alkyl groups (optionally having a ring structure) such as methyl group, ethyl group, isopropyl group, n-propyl group, sec-butyl group, cyclopropyl group, cyclopentyl group, cyclohexyl group, ethylhexyl group, norbornel group, adamantyl group, and benzyl group. The fluorine-containing alkyl group as $R_{12}$ is a group in which hydrogen atoms of the alkyl group have been partially or fully replaced with fluorine atoms.

The group $R_{12}$ containing oxygen atom may be selected from linear ether groups (e.g., methoxymethyl ether (MOM) and methoxyethoxymethyl ether) and cyclic ethers (e.g., tetrahydrofuran and tetrahydropyran). Those ($R_{12}$) of a ring structure having an aromatic ring may be selected from phenyl group and 4-methoxybenzyl group. Those ($R_{12}$) having a carbonyl group may be selected from acetyl group, propylcarbonyl group, pivaloyl group, hexylcarbonyl group, cyclohexylcarbonyl group, tert-butoxycarbonyl group (tert-BOC), benzoyl group, trifluoromethylcarbonyl group, perfluoropropylcarbonyl group, perfluoropivaloyl group, perfluorohexylcarbonyl group, and perfluorocyclohexylcarbonyl group.

The acid-labile protecting group as $R_{12}$ is similarly defined as that of the general formula (1). In other words, it may be selected from alkoxycarbonyl group, acetal group, silyl group, and acyl group. Examples of these groups are those described above. Furthermore, the exemplary groups as the acid-labile protecting groups may be ones in which hydrogen atoms have been partially or fully replaced with fluorine atoms.

The purpose of using the right side repeating unit (a hexafluoroacetone-bonded ester) of the general formula (10) as the another monomer is to improve the polymer in transparency. The purpose of using the acid-labile protecting group is to make the polymer achieve (1) positive type photosensitivity, which is generated by a photoacid generator, and (2) dissolution in basic aqueous solution after irradiation with high-energy beam (e.g., far infrared radiation, excimer laser of 300 nm or less, and X-rays) or electron beam.

The polymer of the present invention can be a fifth copolymer having a repeating unit represented by the general formula (11).

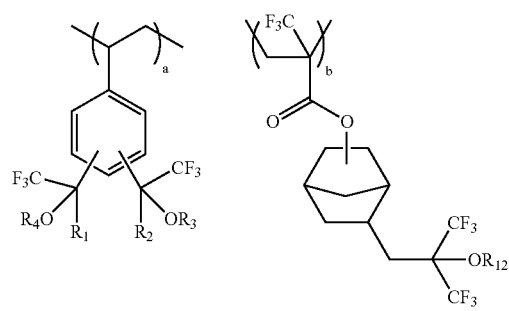

where $R_1$ to $R_4$ are defined as in the general formula (1), $R_{12}$ is defined as in the general formula (10), and "a" and "b" are integers, and "a:b" represents a copolymerization ratio.

The purpose of using the right side repeating unit (an ester having a norbornene skeleton) of the general formula (11) is to provide the polymer with crosslinking property and etching resistance. The resulting polymer can have a high glass transition point and heat resistance for soldering.

The polymer of the present invention can be a sixth copolymer having a repeating unit represented by the general formula (12).

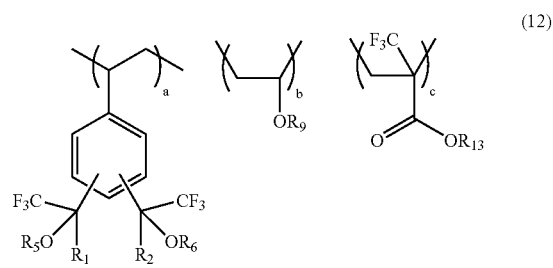

where $R_1$ and $R_2$ are defined as in the general formula (1); $R_5$ and $R_6$ are defined as in the general formula (7); $R_9$ is defined as in the general formula (9); $R_{13}$ is a hydrogen atom or an alkyl or fluorinated alkyl group, the alkyl or fluorinated alkyl group having a carbon atom number of 1–25, having a straight-chain, branched or ring form, and optionally containing at least one of an aromatic ring, oxygen and a carbonyl bond, and "a", "b" and "c" are arbitrary integers, and "a:b:c" represents a copolymerization ratio. In other words, "a", "b" and "c" respectively represent in the sixth copolymer the relative number of the left side repeating units of the general formula (12), that of the central repeating units of the general formula (12), and that of the right side repeating units of the general formula (12). Thus, the sixth copolymer is defined as having these repeating units.

Although the structure of $R_{13}$ is not particularly limited, it is the above-defined functional group other than acid-labile protecting group.

The purpose of using the right side repeating unit (a fluorine-containing methacrylic ester) of the general formula (12) is to provide high transparency within a wavelength range of from vacuum ultraviolet rays to the visible light rays.

The polymer of the present invention can be a seventh copolymer having a repeating unit represented by the general formula (13).

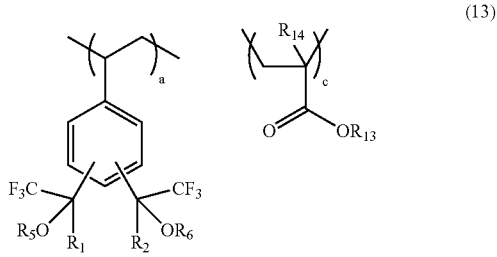

where $R_1$ and $R_2$ are defined as in the general formula (1), $R_5$ and $R_6$ are defined as in the general formula (7), $R_{13}$ is defined as in the general formula (12), $R_{14}$ is a hydrogen atom or methyl group, and "a" and "c" are arbitrary integers, and "a:c" represents a copolymerization ratio.

The purpose of using the right side repeating unit of the general formula (13) is to make the preparation of the copolymer composition easy.

The polymer of the present invention can be an eighth copolymer having a repeating unit represented by the general formula (14).

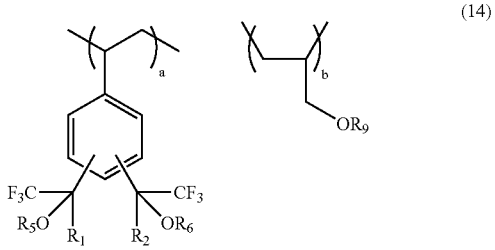

(14)

where $R_1$ and $R_2$ are defined as in the general formula (1), $R_5$ and $R_6$ are defined as in the general formula (7), $R_9$ is defined as in the general formula (9), and "a" and "b" are integers, and "a:b" represents a copolymerization ratio.

It is needless to say that examples of $R_9$ of the general formula (14) may be the same as those of $R_9$ of the general formula (9).

Examples of an allyl ether for forming the right side repeating unit of the general formula (14) are methyl allyl ether, ethyl allyl ether, propyl allyl ether, butyl allyl ether, benzyl allyl ether, and cyclohexyl allyl ether. Further examples of the allyl ether are hydroxyl-containing allyl ethers such as (a) alkylene glycol monoallyl ethers (e.g., ethylene glycol monoallyl ether, propylene glycol monoallyl ether, diethylene glycol monoallyl ether, polyethylene glycol monoallyl ether, and hydroxybutyl allyl ether) and (b) allyl ethers of polyhydric alcohols, such as allyl alcohol and glycerol monoallyl ether. Its further examples are epoxy-containing allyl ethers and β-ketoester-containing allyl ethers such as allyl acetoacetate. Its further examples are fluorine-containing allyl ethers such as trifluoromethyl allyl ether, 2,2,2-trifluoroethyl allyl ether, and 2,2,3,3-tetrafluoropropyl allyl ether. Its further examples are homoallyl ethers and fluorine-containing homoallyl ethers, such as 3-butenyl methyl ether, 3-butenyl methyl ether, 3-butenyl propyl ether, and 1,1,1-trifluoromethyl-3-butenyl methyl ether.

The purpose of using the right side repeating unit (allyl ether) of the general formula (14) is to reduce aromatic rings and carbonyl bonds in the polymer and to make the polymer have a high transparency within a range of from the vacuum ultraviolet rays to the visible light rays. In particular, the purpose of using a fluorine-containing allyl ether or hydroxyl-containing allyl ether is to provide a novel fluorine-containing copolymer that is further improved, for example, in transparency, adhesion to the substrate, and film-forming property.

The polymerization or copolymerization method for obtaining the target polymer (copolymer) is not particularly limited. For example, it is preferable to use radical polymerization or ionic polymerization. In some cases, it is also possible to use coordinated anionic polymerization or living anionic polymerization.

Particulars of the above-mentioned radical polymerization are as follows. The radical polymerization can be conducted by a known manner such as bulk polymerization, solution polymerization, suspension polymerization or emulsion polymerization by a batch-wise, half-continuous or continuous operation.

The radical polymerization initiator is not particularly limited. Its examples are azo compounds, peroxides and redox compounds. Of these, azobisbutyronitrile, t-butylperoxypivalate and benzoyl peroxide are preferable.

The reaction vessel for conducting the polymerization (copolymerization) is not particularly limited. It is optional to use a solvent for conducting the polymerization. The polymerization solvent is preferably one that does not interfere with the radical polymerization. Its typical examples are esters such as ethyl acetate and n-butyl acetate; ketones such as acetone and methyl isobutyl ketone; hydrocarbons such as toluene and cyclohexane; and alcohols such as isopropyl alcohol and ethylene glycol monomethyl ether. Furthermore, it can be selected from various other solvents such as water, ethers, cyclic ethers, fluorohydrocarbons, and aromatic solvents. It is optional to use a single solvent or a mixture of at least two solvents. Furthermore, it is possible to use a molecular weight adjusting agent, such as mercaptan, in the polymerization. The temperature for conducting the polymerization may be suitably adjusted depending on the type of radical polymerization initiator or radical polymerization initiating source. It is preferably 20–200° C., particularly preferably 30–140° C.

After the polymerization, it is possible to remove the reaction medium (i.e., organic solvent or water) from the solution or dispersion of the target polymer by a known method. For example, it can be conducted by reprecipitation followed by filtration, or by heating under vacuum to distill the medium off.

The target polymer according to the present invention may have a number average molecular weight of 1,000–100,000, preferably 3,000–50,000.

The polymer according to the present invention may be formed into a film by dissolving the polymer in a solvent to prepare a coating solution and then by applying the coating solution to a substrate. This solvent is not particularly limited as long as the polymer can be dissolved therein. Its examples are ketones such as acetone, methyl ethyl ketone, cyclohexanone, methyl isoamyl ketone and 2-heptanone; polyhydric alcohols such as ethylene glycol, ethylene glycol monoacetate, diethylene glycol, diethylene glycol monoacetate, propylene glycol, propylene glycol monoacetate, dipropylene glycol, and ethers (monomethyl ether, monoethyl ether, monopropyl ether, monobutyl ether and monophenyl ether) of dipropylene glycol monoacetate, and derivatives of polyhydric alcohols; cyclic ethers such as dioxane; esters such as methyl lactate, ethyl lactate, methyl acetate, ethyl acetate, butyl acetate, methyl pyruvate, ethyl pyruvate, methyl methoxypropionate, and ethyl ethoxypropionate; aromatic solvents such as xylene and toluene; and fluorine-containing solvents such as fleon, alternative fleon, perfluoro compounds, and hexafluoroisopropyl alcohol. Furthermore, it is possible to use a high-boiling-point, weak solvent (e.g., a terpene-based petroleum naphtha solvent or paraffinic solvent) for the purpose of increasing coatability (applicability of the coating solution). The solvent for preparing the coating solution may be a single solvent or a mixture of at least two solvents.

It is possible to form an anti-reflection film on the surface of a substrate (e.g., glass, plastic, liquid crystal panel, plasma display panel, and electroluminescence panel) by applying the polymer of the present invention thereto to have an ultra-thin thickness. The anti-reflection film can be a single layer of this polymer or a laminate of at least one layer of this polymer and at least one layer of another material having a refractive index different from that of this polymer. In order to enhance its anti-reflection capability, it is preferable to adjust refractive index of the polymer in a visible light region to 1.42 or lower, more preferably 1.4 or lower. As the fluorine content of the polymer increases, the refractive index becomes lower. With higher fluorine content, its adhesion to substrate tends to lower. In this case, it is possible to increase adhesion by using an anti-reflection film prepared by polymerizing a monomer that is represented by the general formula (1) or (2) and that has an alcohol side chain in which $R_3$ is a hydrogen. The thickness of the anti-reflection film may be varied depending on the refractive index of the substrate. It may be in a range of 50–200 nm.

It is possible to produce a novel resist composition by using the polymer according to the present invention. It is the most preferable to use this polymer for producing a positive-type resist composition. In fact, this resist composition contains (a) a polymer according to the present invention, of which solubility in alkali aqueous solution changes by the action of acid, and (b) an acid generator. This resist composition is preferably used, for example, for preparing semiconductors using a 248 nm KrF or 193 nm ArF excimer laser or a vacuum ultraviolet (typically 157 nm) $F_2$ laser. In fact, the polymer, of which solubility in alkali aqueous solution changes by the action of acid, is characterized in that at least one of $R_3$ and $R_4$ in the general formulas (1)–(2) is an acid-labile protecting group. This polymer is not further particularly limited in its structure. This polymer can be prepared by using a monomer (represented by one of the general formulas (1)–(2)) in which at least one of $R_3$ and $R_4$ as an acid-labile protecting group(s) is defined as having a linear ether group (such as tert-butyl group, tert-butoxycarbonyl group, methoxy methyl ether or ethoxy methyl ether) or a lactone group containing a cyclic structure and is defined as being a functional group in which its ester moiety is severed by acid. The above polymer is insoluble or very slightly soluble in alkali aqueous solution prior to the activating energy ray irradiation. The activating energy ray irradiation, however, generates an acid from the acid generator. Then, the polymer is hydrolyzed by this acid and thereby becomes soluble in alkali aqueous solution.

The above-mentioned acid generator for a resist composition is not particularly limited. It can be suitably selected from acid generators for chemically amplified resists. Examples of such acid generators are bissulfonyldiazomethanes, nitrobenzyl derivatives, onium salts, halogen-containing triazine compounds, cyano group-containing oximesulfonate compounds, and other oximsulfonate compounds. The acid generator may be used in the form of a single compound or a mixture of at least two compounds. The content of the acid generator in the resist composition may be 0.5–20 parts by weight, relative to 100 parts by weight of the polymer. If it is less than 0.5 parts by weight, the resist composition may become insufficient in image forming capability. If it is greater than 20 parts by weight, it may become difficult to prepare a uniform solution of the resist composition. Thus, the resulting solution may become inferior in storage stability.

The above-mentioned resist composition according to the present invention can be used in conventional resist patterning methods, as exemplified in the following. Firstly, a solution of the resist composition is applied to a supporting member (e.g., silicon wafer) by spin coating or the like, followed by drying to form a photosensitive layer. Then, the photosensitive layer is exposed to an excimer laser light from an exposure apparatus through a desired mask pattern, followed by heating. Then, a development treatment is conducted by using, for example, an alkali aqueous solution such as 0.1–10 wt % tetranmethylammonium hydroxide aqueous solution, thereby obtaining a resist pattern conforming to the mask pattern.

According to need, it is optional to add a miscible additive to the polymer. Examples of such additive are additional resins, quencher, plasticizer, stabilizer, coloring agent, surfactant, tackifier, leveling agent, deforming agent, compatibility enhancing agent, adhesion enhancing agent, and antioxidant.

The following nonlimitative examples are illustrative of the present invention.

EXAMPLE 1

Production of Styrene Derivative (3,5-D-HFA-ST) Represented by the Formula (3)

A styrene derivative (hereinafter 3,5-D-HFA-ST) represented by the formula (3) was synthesized by the following steps (a), (b) and (c).

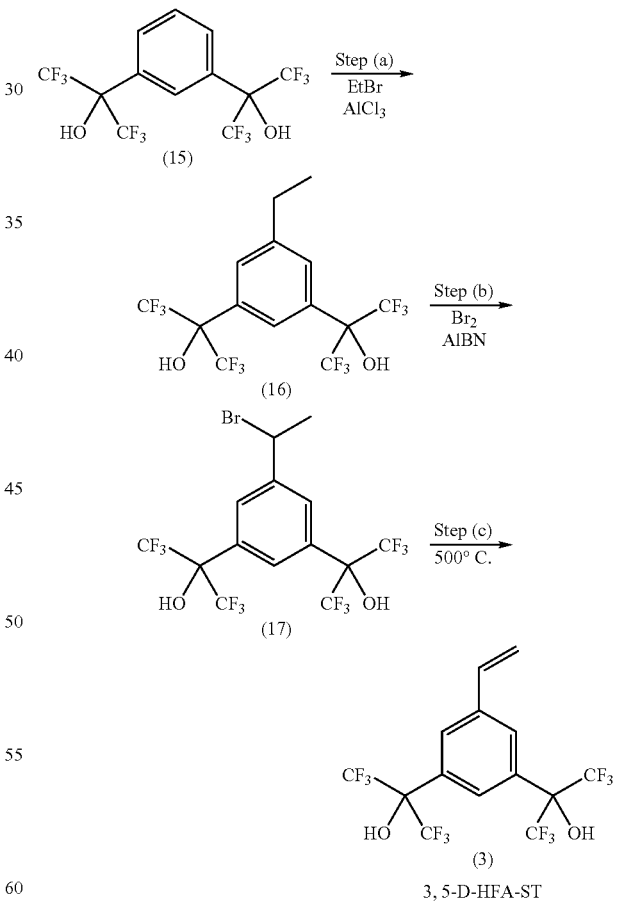

Step (a): Ethylation of Benzene Derivative

A three necked flask equipped with a reflux condenser, a dropping funnel and a stirrer was charged with 100 g of a benzene derivative (hereinafter 1,3-Bis-HFAB) represented by the formula (15) and 83 g of anhydrous aluminum chloride, followed by heating in oil bath of 50° C. 133 g of ethyl bromide were added in a dropwise manner from the dropping funnel by spending 5 hr. After the reaction, the reaction solution was added to 500 ml of iced water. A black-color oil-like substance precipitated in the lower layer was taken out and then washed with water. This product was subjected to a distillation under vacuum, thereby obtaining 30 g of an ethyl benzene derivative represented by the formula (16). This benzene derivative was found to have the following properties.

Boiling point: 80–84° C./2 mmHg NMR:$^1$H-NMR (TMS, CDCl$_3$): 1.28 (t, 7.2 Hz, 3H), 2.75 (q, 7.2 Hz, 2H), 7.66 (s, 2H), 7.92 (S, 1H)

Step (b) Bromination of Ethyl Benzene Derivative

A three-necked flask equipped with a reflux condenser, a dropping funnel, and a stirrer was charged with 25 g of the ethyl benzene derivative (of the formula (16)) obtained in the step (a), 10 g of bromine, and 0.1 g of AIBN, followed by heating for 7 hr in oil bath of 60° C. After the reaction, the reaction solution was put into a separating funnel, followed by washing with 5% sodium thiosulfate aqueous solution. The resulting product was subjected to a distillation under vacuum, thereby obtaining 22 g of a brominated compound represented by the formula (17). This brominated compound was found to have the following properties.

Boiling point: 110–115° C./2 mmHg $^1$H-NMR (TMS, CDCl$_3$): 2.07 (d, 6.8 Hz, 3H), 5.23 (q, 6.8 Hz, 1H), 7.92 (s, 2H), 8.00 (S, 1H)

Step (c): Pyrolysis of Brominated Compound

A quartz tube (inner diameter: 20 mm) charged with ceramic Raschig rings was set in a vertical, tubular, electric furnace. The quartz tube was connected at its top with a dropping funnel and at its bottom with a trap cooled with a refrigerant (a mixture of dry ice and methanol). Furthermore, a vacuum pump was connected to an outlet of the trap. Then, 10 g of the brominated compound (of the formula (17)) obtained in the step (b) were put into the dropping funnel. The pressure of the atmosphere of the apparatus was reduced to about 5 mmHg, and the quartz tube was heated to about 500° C. Then, the brominated compound (of the formula (17) was added to the quartz tube in a dropwise manner at a rate of about 0.5 g/min for its pyrolysis. The target styrene derivative of the formula (3) was collected in an amount of 7 g in the trap. This styrene derivative was found to have the following properties.

$^1$H-NMR (TMS, CDCl$_3$): 3.56 (s, 2H), 5.40 (d, 11.2 Hz, 1H), 5.85 (d, 17.6 Hz, 1H), 6.76 Hz (dd, 17.6 Hz, 11.2 Hz, 1H), 7.84 (s, 2H), 7.96 (S, 1H) GC-MS (EI method): m/e 436 (M$^+$), 367 (M$^+$-CF$_3$)

EXAMPLE 2

Homopolymerization of 3,5-D-HFA-ST

A three-necked flask equipped with a reflux condenser and a stirrer was charged with 10 g of 3,5-D-HFA-ST (see the formula below), 0.2 g of AIBN (a polymerization initiator), and 40 g of n-butyl acetate (a polymerization solvent), followed by heating in oil bath of 60° C.

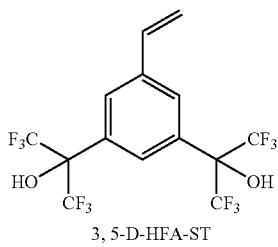

3, 5-D-HFA-ST

Under this condition, the reaction was conducted for 20 hr. After that, 1 liter of n-hexane was added to the reaction solution, followed by stirring. The resulting precipitate was separated by filtration and then dried under vacuum at 50° C. for 18 hr. The obtained polymer composition was determined by $^1$H-NMR and $^{19}$F-NMR. Its weight average molecular weight (Mw) and number average molecular weight (Mn) were determined by gel permeation chromatography (GPC) using polystyrene as a standard. The results are shown in Table.

TABLE

| Ex. | Charged Monomers (g) | Yield (g) | Polymer Composition (3,5-D-HFA-ST/Comonomer(s)) | Mn | Mw | Mw/Mn |
|---|---|---|---|---|---|---|
| 2 | 3,5-D-HFA-ST(10 g)/- | 4.8 | 100/0 | 8,000 | 13,600 | 1.7 |
| 3 | 3,5-D-HFA-ST(10 g)/3,5-D-HFA-ST-BOC(8 g) | 13.6 | 42/58 | 9,000 | 17,100 | 1.9 |
| 4 | 3,5-D-HFA-ST(10 g)/3,5-D-HFA-ST-TFET(7 g)/MA-MAD(6.5 g) | 14.5 | 31/29/40 | 9,600 | 17,300 | 1.8 |
| 5 | 3,5-D-HFA-ST(10 g)/4-HFA-ST(6.2 g) | 10.9 | 48/52 | 9,200 | 14,700 | 1.6 |
| 6 | 3,5-D-HFA-ST(10 g)/MA-HTIP(5.4 g) | 10.0 | 59/41 | 9,500 | 16,100 | 1.7 |
| 7 | 3,5-D-HFA-ST(10 g)/TFMA-B(0.5 g) | 8.3 | 54/46 | 8,800 | 15,800 | 1.8 |
| 8 | 3,5-D-HFA-ST(10 g)/TFMA-MAD(6.6 g) | 5.8 | 65/35 | 6,200 | 10,500 | 1.7 |
| 9 | 3,5-D-HFA-ST-TFET(10 g)/TFMA-B(0.5 g) | 9.1 | 52/48 | 9,200 | 16,000 | 1.7 |
| 10 | 3,5-D-HFA-ST(10 g)/TFMA-BTHB-NB-BOC*5.0 g) | 6.4 | 58/42 | 8,900 | 14,200 | 1.6 |
| 11 | 3,5-D-HFA-ST-BOC(10 g)/TFMA-BTHB-NB(5.0 g) | 6.1 | 60/40 | 7,000 | 11,200 | 1.6 |
| 12 | 3,5-D-HFA-ST-BOC(10 g)/TFMA-H-3,5-D-HFA-PH(8.5 g)/H-HQ-VE (3.0 g) | 10.3 | 30/45/25 | 7,000 | 11,200 | 1.6 |
| 13 | 3,5-D-HFA-ST-BOC(10 g)/TFMA-B(9.0 g)/TFE-VE(2.9 g) | 15.0 | 33/47/20 | 14,000 | 27,800 | 2.0 |
| 14 | 3,5-D-HFA-ST(10 g)/A-B(6.0 g)/HFIB(5.0 g) | 17.4 | 32/47/21 | 13,100 | 19,500 | 1.5 |
| 15 | 3,5-D-HFA-ST-BOC(10 g)/A-TFE(9.0 g)/HFIB(5.0 g) | 13.2 | 37/44/19 | 11,700 | 21,000 | 1.8 |
| 16 | 3,5-D-HFA-ST(10 g)/A-CN(7.2 g)/HFIB(4.8 g) | 16.3 | 35/43/22 | 9,600 | 17,300 | 1.8 |
| 17 | 3,5-D-HFA-ST-MOM(10 g)/A-OFCPE(10 g) | 5.2 | 48/52 | 9,800 | 18,600 | 1.9 |
| 18 | 3,5-D-HFA-ST-MOM(10 g)/HBAE(5.0 g)/A-OFCPE(10.0 g) | 17.8 | 37/21/51 | 8,500 | 13,600 | 1.6 |

EXAMPLE 3

Copolymerization of 3,5-D-HFA-ST & 3,5-D-HFA-ST-BOC

Example 2 was repeated except in that 10 g of 3,5-D-HFA-ST and 8.0 g of 3,5-D-HFA-ST-BOC (represented by the following formulas) were used as the monomers in place of 10 g of 3,5-D-HFA-ST. The results are shown in Table.

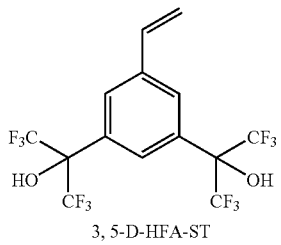

3, 5-D-HFA-ST

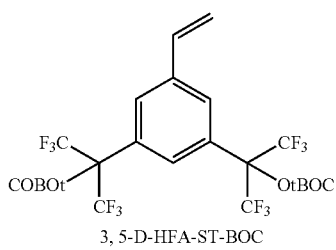

3, 5-D-HFA-ST-BOC

EXAMPLE 4

Copolymerization of 3,5-D-HFA-ST & 3,5-D-HFA-ST-TFET & MA-MAD

Example 2 was repeated except in that 10 g of 3,5-D-HFA-ST and 7 g of 3,5-D-HFA-ST-TFET and 6.5 g of MA-MAD (represented by the following formulas) were used as the monomers in place of 10 g of 3,5-D-HFA-ST. The results are shown in Table.

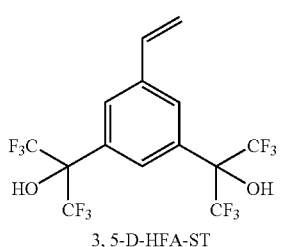

3, 5-D-HFA-ST

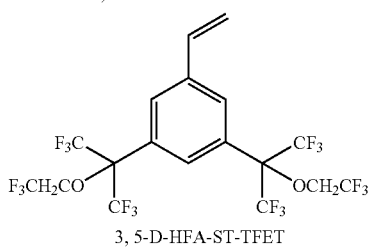

3, 5-D-HFA-ST-TFET

-continued

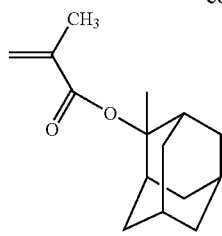

MA-MAD

EXAMPLE 5

Copolymerization of 3,5-D-HFA-ST & 4-HFA-ST

Example 2 was repeated except in that 10 g of 3,5-D-HFA-ST and 6.2 g of 4-HFA-ST (represented by the following formulas) were used as the monomers in place of 10 g of 3,5-D-HFA-ST. The results are shown in Table.

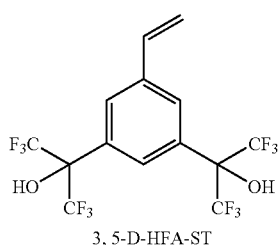

3, 5-D-HFA-ST

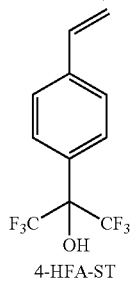

4-HFA-ST

EXAMPLE 6

Copolymerization of 3,5-D-HFA-ST & MA-HFIP

Example 2 was repeated except in that 10 g of 3,5-D-HFA-ST and 5.4 g of MA-HFIP (represented by the following formulas) were used as the monomers in place of 10 g of 3,5-D-HFA-ST. The results are shown in Table.

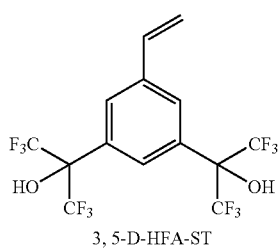

3, 5-D-HFA-ST

-continued

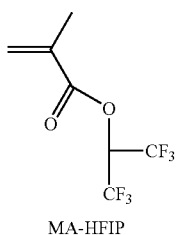

MA-HFIP

-continued

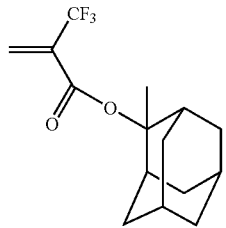

TFMA-MAD

EXAMPLE 7

Copolymerization of 3,5-D-HFA-ST & TFMA-B

Example 2 was repeated except in that 10 g of 3,5-D-HFA-ST and 5.0 g of TFMA-B (represented by the following formulas) were used as the monomers in place of 10 g of 3,5-D-HFA-ST. The results are shown in Table.

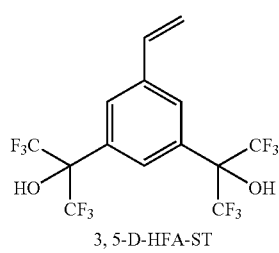

3, 5-D-HFA-ST

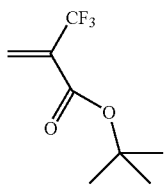

TFMA-B

EXAMPLE 8

Copolymerization of 3,5-D-HFA-ST & TFMA-MAD

Example 2 was repeated except in that 10 g of 3,5-D-HFA-ST and 6.6 g of TFMA-MAD (represented by the following formulas) were used as the monomers in place of 10 g of 3,5-D-HFA-ST. The results are shown in Table.

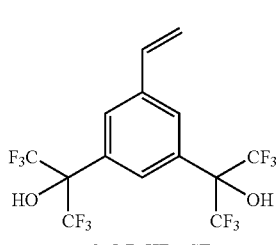

3, 5-D-HFA-ST

EXAMPLE 9

Copolymerization of 3,5-D-HFA-TFET & TFMA-B

Example 2 was repeated except in that 10 g of 3,5-D-HFA-ST-TFET and 5.0 g of TFMA-B (represented by the following formulas) were used as the monomers in place of 10 g of 3,5-D-HFA-ST. The results are shown in Table.

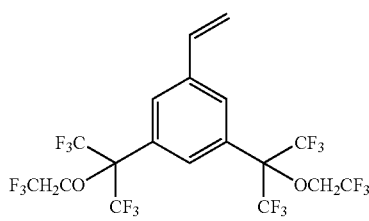

3, 5-D-HFA-ST-TFET

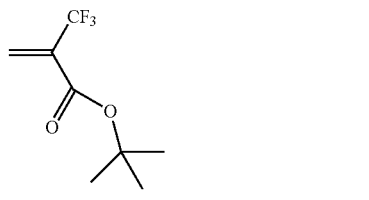

TFMA-B

EXAMPLE 10

Copolymerization of 3,5-D-HFA-ST & TFMA-BTHB-NB-BOC

Example 2 was repeated except in that 10 g of 3,5-D-HFA-ST and 5.0 g of TFMA-BTHB-NB-BOC (represented by the following formulas) were used as the monomers in place of 10 g of 3,5-D-HFA-ST. The results are shown in Table.

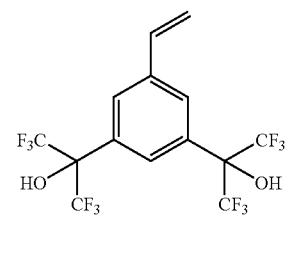

3,5-D-HFA-ST

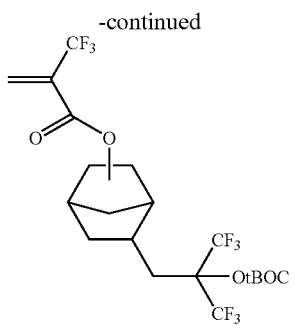

TFMA-BTHB-NB-BOC

EXAMPLE 11

Copolymerization of 3,5-D-HFA-ST-BOC & TFMA-BTHB-NB

Example 2 was repeated except in that 10 g of 3,5-D-HFA-ST-BOC and 5.0 g of TFMA-BTHB-NB (represented by the following formulas) were used as the monomers in place of 10 g of 3,5-D-HFA-ST. The results are shown in Table.

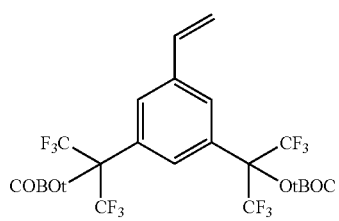

3,5-D-HFA-ST

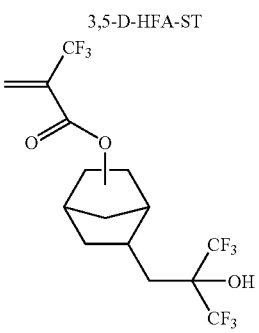

TFMA-BTHB-NB

EXAMPLE 12

Copolymerization of 3,5-D-HFA-ST-BOC & TFMA-H-3,5-D-HFA-PH & H-HQ-VE

Example 2 was repeated except in that 10 g of 3,5-D-HFA-ST-BOC, 8.5 g of TFMA-H-3,5-D-HFA-PH & 3.0 g of H-HQ-VE (represented by the following formulas) were used as the monomers in place of 10 g of 3,5-D-HFA-ST. The results are shown in Table.

3,5-HFA-ST-BOC

TFMA-H-3,5-D-HFA-PH

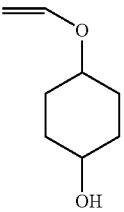

H-HQ-VE

EXAMPLE 13

Copolymerization of 3,5-D-HFA-ST-BOC & TFMA-B & TFE-VE

Example 2 was repeated except in that 10 g of 3,5-D-HFA-ST-BOC, 9.0 g of TFMA-B and 2.9 g of TFE-VE (represented by the following formulas) were used as the monomers in place of 10 g of 3,5-D-HFA-ST. The results are shown in Table.

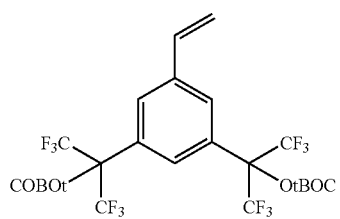

3,5-D-HFA-ST-BOC

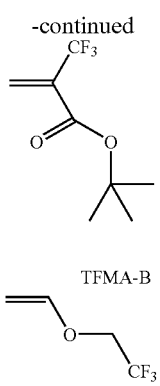

TFMA-B

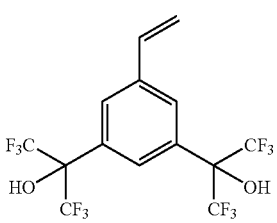

TFE-VE

EXAMPLE 14

Copolymerization of 3,5-D-HFA-ST & A-B & HFIB

Example 2 was repeated except in that 10 g of 3,5-D-HFA-ST, 6.0 g of A-B and 5.0 g of HFIB (represented by the following formulas) were used as the monomers in place of 10 g of 3,5-D-HFA-ST. The results are shown in Table.

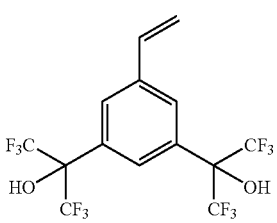

3,5-D-HFA-ST

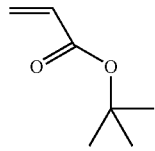

A-B

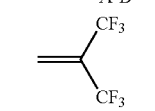

HFIB

EXAMPLE 15

Copolymerization of 3,5-D-HFA-ST-BOC & A-TFE & HFIB

Example 2 was repeated except in that 10 g of 3,5-D-HFA-ST-BOC, 9.0 g of A-TFE and 5.0 g of HFIB (represented by the following formulas) were used as the monomers in place of 10 g of 3,5-D-HFA-ST. The results are shown in Table.

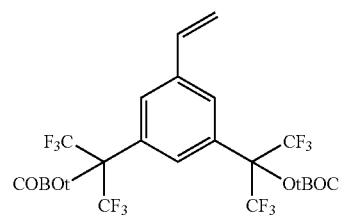

3,5-D-HFA-BOC-ST

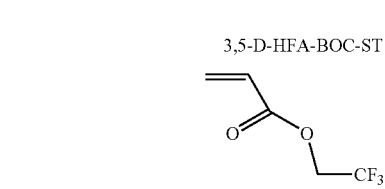

A-TFE

HFIB

EXAMPLE 16

Copolymerization of 3,5-D-HFA-ST & A-CN & HFIB

Example 2 was repeated except in that 10 g of 3,5-D-HFA-ST, 7.2 g of A-CN and 4.8 g of HFIB (represented by the following formulas) were used as the monomers in place of 10 g of 3,5-D-HFA-ST. The results are shown in Table.

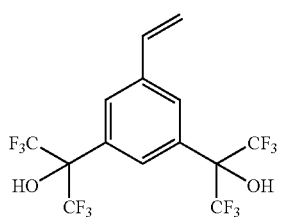

3,5-D-HFA-ST

A-CN

HFIB

EXAMPLE 17

Copolymerization of 3,5-D-HFA-ST-MOM & A-OFCPE

Example 2 was repeated except in that 10 g of 3,5-D-HFA-ST-MOM and 10 g of A-OFCPE (represented by the following formulas) were used as the monomers in place of 10 g of 3,5-D-HFA-ST. The results are shown in Table.

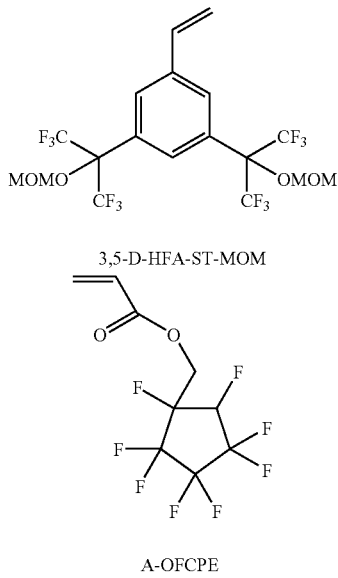

3,5-D-HFA-ST-MOM

A-OFCPE

EXAMPLE 18

Copolymerization of 3,5-HFA-ST-MOM & HB-AE & A-OFCPE

Example 2 was repeated except in that 10 g of 3,5-HFA-ST-MOM, 5.0 g of HB-AE and 10 g of A-OFCPE (represented by the following formulas) were used as the monomers in place of 10 g of 3,5-D-HFA-ST. The results are shown in Table.

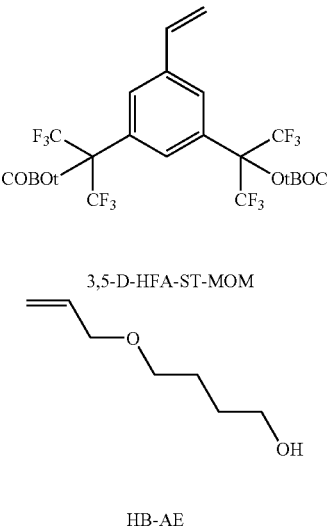

3,5-D-HFA-ST-MOM

HB-AE

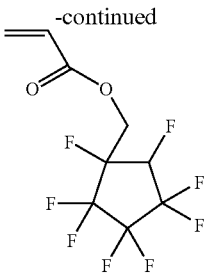

A-OFCPE

EXAMPLE 19

100 parts by weight of the copolymer obtained in Example 4 were dissolved in methyl isobutyl ketone so that the resulting solution had a solid matter concentration of about 30%. The resulting coating liquid was applied to a glass plate to form thereon a film of 50 μm thickness. The film was subjected to a natural drying for 1 hr and then to a compulsory drying at 100° C. for 30 min with a hot air dryer to accelerate the crosslinking reaction. The resulting dried film was measured for refractive index using Abbe's refractometer. The result was 1.376.

Separately, the above solution (having a solid matter concentration of about 30%) was diluted to have a solid matter concentration of about 2%. The resulting solution was applied to a glass substrate by spin coating. The resulting film was subjected to a heat treatment at 100° C. for 3 min and then was found to have a thickness of 103 nm. The resulting coated glass was measured for reflectance at a wavelength of 650 nm. With this, the result was 0.9%, showing a sufficient anti-reflection property.

EXAMPLE 20

The copolymers obtained in Examples 5 and 6 were dissolved in propylene glycol monomethyl acetate to have a solid matter concentration of 14%. Then, an acid generator, triphenylsulfonium triflate (TPS105) made by Midori Kagaku Co., Ltd., was dissolved in an amount of 2 parts by weight per 100 parts by weight of each copolymer, thereby preparing resist solutions of Examples 5–6. These resist solutions were applied to substrates by spin coating. The resulting resist films were found to have light transmittances of 71% and 69% in Examples 5–6 respectively at a wavelength of 157 nm and at a film thickness of 100 nm, showing high transparency in vacuum ultraviolet wavelength region.

Then, the above resist solutions were filtered with a membrane filer (pore diameter: 0.2 micrometers). The resulting resist solutions were applied to silicon wafers by spin coating to form resist films each having a thickness of 250 nm. Then, the resist films were subjected to a preliminary baking at 110° C., followed by exposure at 248 nm using a KrF excimer laser micro scanner and then by a post exposure baking at 120° C. Then, the resist films were developed at 23° C. for 1 minute using 2.38 wt % tetramethylammonium hydroxide aqueous solution to form resist patterns. Each resist pattern had a high resolution and almost no development defects.

The entire disclosure of Japanese Patent Application Nos. 2001-380776 (filed on Dec. 13, 2001) and 2002-125505

(filed on Apr. 26, 2002), including specification, drawings, claims and summary, is incorporated herein by reference in its entirety.

What is claimed is:

1. A fluorine-containing polymerizable monomer having a structure of the general formula (1),

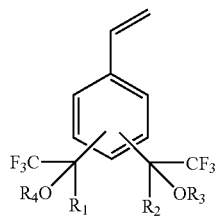

(1)

where each of $R_1$ and $R_2$ is independently a methyl group or trifluoromethyl group, and each of $R_3$ and $R_4$ is independently a hydrogen atom, an alkyl group, a fluorinated alkyl group, a ring structure having an aromatic ring, or an acid-labile protecting group, each of the alkyl group and the fluorinated alkyl group independently having a straight-chain, branched or ring form and having a carbon atom number of 1–25, each of $R_3$ and $R_4$ optionally and independently containing at least one of an oxygen atom and a carbonyl bond.

2. A monomer according to claim 1, which has a structure of the general formula (2),

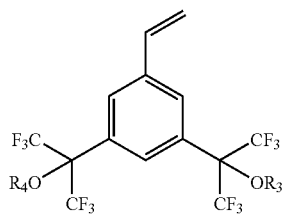

(2)

where $R_3$ and $R_4$ are defined as in the general formula (1).

3. A monomer according to claim 1, which has a structure of the following general formula (3).

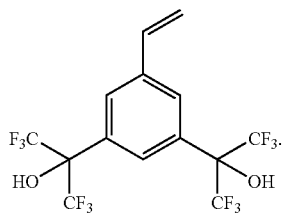

(3)

4. A monomer according to claim 1, wherein each of $R_3$ and $R_4$ is independently a hydrogen atom, an alkyl group, a fluorinated alkyl group, or a ring structure having an aromatic ring, each of the alkyl group and the fluorinated alkyl group independently having a straight-chain, branched or ring form and having a carbon atom number of 1–25, each of $R_3$ and $R_4$ optionally and independently containing at least one of an oxygen atom and a carbonyl bond.

5. A polymer prepared by polymerizing or copolymerizing a monomer according to claim 1.

6. A polymer according to claim 5, which has a polydispersity index of 1.5 to 2.0.

7. A polymer according to claim 5, comprising a repeating unit represented by the general formula (7),

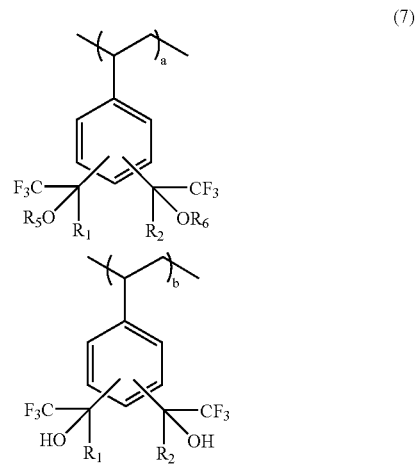

(7)

where $R_1$ and $R_2$ are defined as in the general formula (1), $R_5$ and $R_6$ are identical with $R_3$ and $R_4$ of the general formula (1) and optionally contain at least one of an oxygen atom and a carbonyl bond, at least one of $R_5$ and $R_6$ being the acid-labile protecting group, "a" and "b" are arbitrary integers, and "a b" represents a: copolymerization ratio.

8. A polymer according to claim 5, comprising a repeating unit represented by the general formula (8),

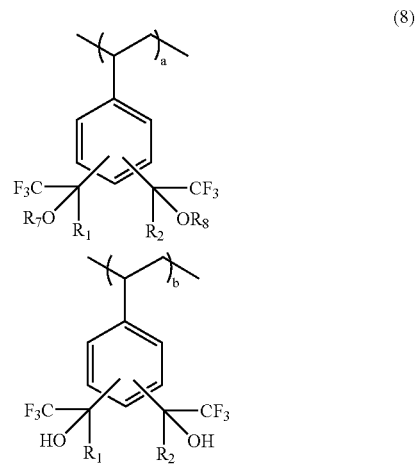

(8)

where $R_1$ and $R_2$ are defined as in the general formula (1), $R_7$ and $R_8$ are identical with $R_3$ and $R_4$ of the general formula (1) and optionally contain at least one of an aromatic ring, an oxygen atom and a carbonyl bond, each of $R_7$ and $R_8$ being the acid-labile protecting group, the alkyl group or the fluorinated alkyl group, at least one of $R_7$ and $R_8$ being the alkyl group or the fluorinated alkyl group, and "a" and "b" are arbitrary integers, and "a:b" represents a copolymerization ratio.

9. A polymer according to claim 5, wherein the polymer is prepared by copolymerizing a monomer according to claim 1 with another monomer that is at least one selected from the group consisting of acrylic esters, methacrylic esters, fluorine-containing acrylic esters, fluorine-containing methacrylic esters, styrene, styrene derivatives, fluorine-containing styrene derivatives, vinyl ethers, fluorine-containing vinyl ethers, olefins, fluorine-containing olefins, norbornene, norbornene derivatives, and fluorine-containing norbornene derivatives.

10. A polymer according to claim 5, comprising a repeating unit represented by the general formula (9),

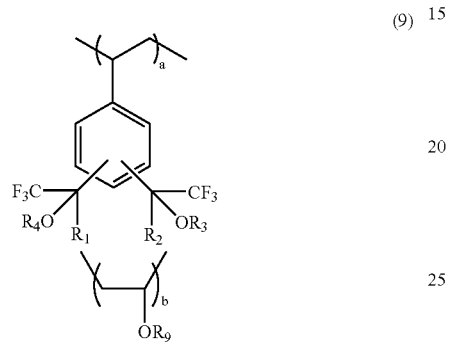

(9)

where $R_1$ to $R_4$ are defined as in the general formula (1), $R_9$ is an alkyl or fluorinated alkyl group having a carbon atom number of 1–25, having a straight-chain, branched or ring form, and optionally containing at least one of an aromatic ring, oxygen and a carbonyl bond, and "a" and "b" are arbitrary integers, and "a:b" represents a copolymerization ratio.

11. A polymer according to claim 5, comprising a repeating unit represented by the general formula (10),

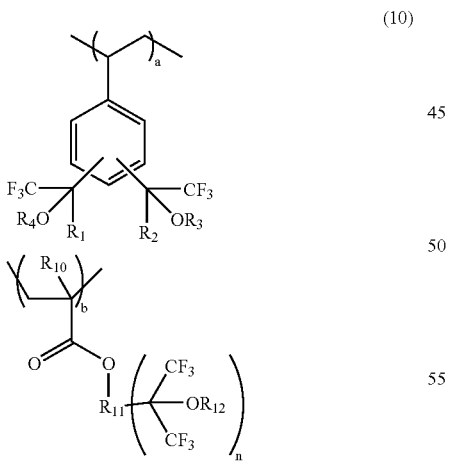

(10)

where $R_1$ to $R_4$ are defined as in the general formula (1), $R_{10}$ is a hydrogen atom, methyl group or trifluoromethyl group, $R_{11}$ is an alkyl group or a ring structure and optionally contains at least one of fluorine, oxygen and a carbonyl bond, the alkyl group having a carbon atom number of 1–25 and having a straight-chain, branched or ring form, the ring structure having an aromatic ring, $R_{12}$ is a hydrogen atom, an alkyl or fluorinated alkyl group or an acid-labile protecting group, the alkyl or fluorinated alkyl group having a carbon atom number of 1–25, having a straight-chain, branched or ring form, $R_{12}$ optionally containing at least one of an aromatic ring, oxygen and a carbonyl bond, "a" and "b" are arbitrary integers, and "a:b" represents a copolymerization ratio, and "n" is an integer of 1–3.

12. A polymer according to claim 11, comprising a repeating unit represented by the following general formula (11),

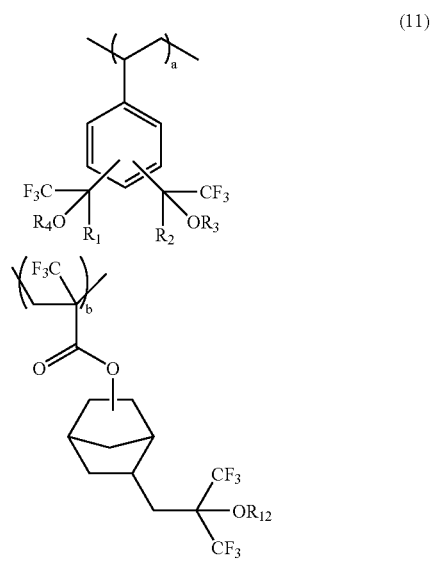

(11)

where $R_1$ to $R_4$ are defined as in the general formula (1), $R_{12}$ is defined as in the general formula (10), and "a" and "b" are integers, and "a:b" represents a copolymerization ratio.

13. A polymer according to claim 5, comprising a repeating unit represented by the general formula (12),

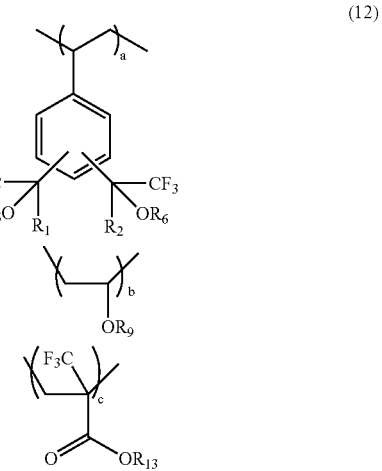

(12)

where $R_1$ and $R_2$ are defined as in the general formula (1); $R_5$ and $R_6$ are identical with $R_3$ and $R_4$ of the general formula (1) and optionally contain at least one of an oxygen atom and a carbonyl bond, at least one of $R_5$ and $R_6$ being the acid-labile protecting group, $R_9$ is an alkyl or fluorinated alkyl group having a carbon atom number of 1–25, having a straight-chain, branched or ring form, and optionally containing at least one of an aromatic ring, oxygen and a carbonyl bond, $R_{13}$ is a hydrogen atom or an alkyl or fluorinated alkyl group, the alkyl or fluorinated alkyl group having a carbon atom number of 1–25, having a straight-chain, branched or ring form, and optionally containing at least one of an aromatic ring, oxygen and a carbonyl bond, and "a", "b" and "c" are arbitrary integers, and "a:b:c" represents a copolymerization ratio.

14. A polymer according to claim 5, comprising a repeating unit represented by the general formula (13),

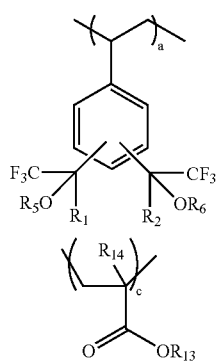

(13)

where $R_1$ and $R_2$ are defined as in the general formula (1), $R_5$ and $R_6$ are identical with $R_3$ and $R_4$ of the general formula (1) and optionally contain at least one of an oxygen atom and a carbonyl bond, at least one of $R_5$ and $R_6$ being the acid-labile protecting group, $R_{13}$ is a hydrogen atom or an alkyl or fluorinated alkyl group, the alkyl or fluorinated alkyl group having a carbon atom number of 1–25, having a straight-chain, branched or ring form, and optionally containing at least one of an aromatic ring, oxygen and a carbonyl bond, $R_{14}$ is a hydrogen atom or methyl group, and "a" and "c" are arbitrary integers, and "a:c" represents a copolymerization ratio.

15. A polymer according to claim 5, comprising a repeating unit represented by the general formula (14),

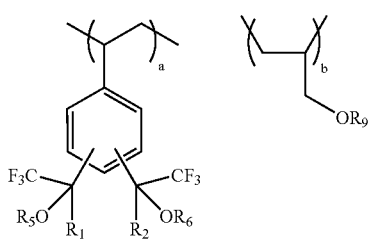

(14)

where $R_1$ and $R_2$ are defined as in the general formula (1), $R_5$ and $R_6$ are identical with $R_3$ and $R_4$ of the general formula (1) and optionally contain at least one of an oxygen atom and a carbonyl bond, at least one of $R_5$ and $R_6$ being the acid-labile protecting group, $R_9$ is an alkyl or fluorinated alkyl group having a carbon atom number of $_{1-25}$, having a straight-chain, branched or ring form, and optionally containing at least one of an aromatic ring, oxygen and a carbonyl bond, and "a" and "b" are integers, and "a:b" represents a copolymerization ratio.

16. An anti-reflection coating material comprising a polymer according to claim 5.

17. A resist composition comprising a polymer according to claim 5.

18. A process for producing a monomer having a structure of the general formula (1),

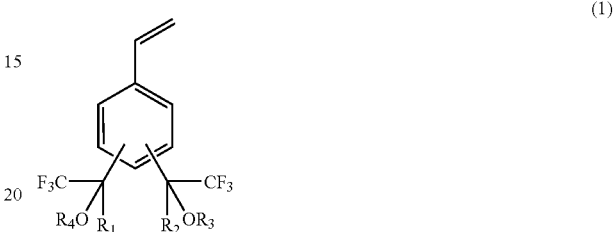

(1)

where each of $R_1$ and $R_2$ is independently a methyl group or trifluoromethyl group, and each of $R_3$ and $R_4$ is independently a hydrogen atom, an alkyl group, a fluorinated alkyl group, a ring structure having an aromatic ring, or an acid-labile protecting group, each of the alkyl group and the fluorinated alkyl group independently having a straight-chain, branched or ring form and having a carbon atom number of 1–25, each of $R_3$ and $R_4$ optionally and independently containing at least one of an oxygen atom and a carbonyl bond, comprising the step of introducing a vinyl group into a benzene ring of a benzene derivative represented by the general formula (4),

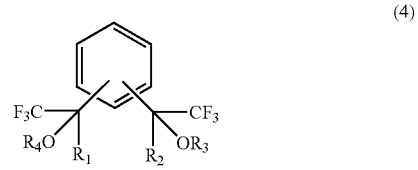

(4)

where $R_1$ to $R_4$ are defined as in the general formula (1).

19. A process for producing a monomer having a structure of the general formula (1),

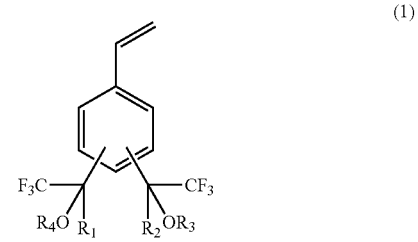

(1)

where each of $R_1$ and $R_2$ is independently a methyl group or trifluoromethyl group, and each of $R_3$ and $R_4$ is independently a hydrogen atom, an alkyl group, a fluorinated alkyl group, a ring structure having an aromatic ring, or an acid-labile protecting group, each of the alkyl group and the fluorinated alkyl group independently having a straight-chain, branched or ring form and having a carbon atom number of 1–25, each of $R_3$ and $R_4$ optionally and independently containing at least one of an oxygen atom and a carbonyl bond, comprising the steps of:

(a) reacting a benzene derivative, represented by the general formula (4), with an ethylation agent in the presence of a Lewis acid catalyst or protonic acid catalyst, thereby producing an ethyl benzene derivative represented by the general formula (5);

(b) reacting the ethyl benzene derivative with bromine, thereby producing a compound represented by the general formula (6); and (c) pyrolyzing the compound of the general formula (6) into the monomer of the general formula (1),

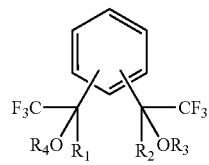

(4)

where $R_1$ to $R_4$ of the general formulas (4)–(6) are defined as in the general formula (1).

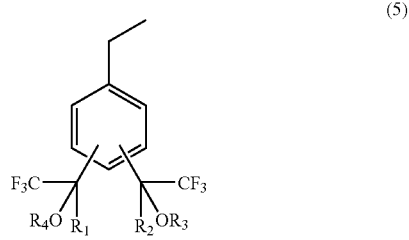

(5)

20. A process according to claim 19, wherein the benzene derivative of the general formula (4) is 1,3-bis(hexafluoro-2-hydroxy-2-propyl)benzene.

21. A process according to claim 19, wherein the ethylation agent of the step (a) is ethyl bromide.

22. A process according to claim 19, wherein the step (b) is conducted in the presence of a radical initiator.

* * * * *